US010307066B2

(12) United States Patent
Jeon et al.

(10) Patent No.: US 10,307,066 B2
(45) Date of Patent: Jun. 4, 2019

(54) MEASURING APPARATUS AND WEARABLE DEVICE COMPRISING SAME (71) Applicant: LG ELECTRONICS INC., Seoul (KR)

(72) Inventors: Seongman Jeon, Seoul (KR); Wonhyeog Jin, Seoul (KR); Hyoungkil Yoon, Seoul (KR)

(73) Assignee: LG Electronics Inc., Seoul (KR)

(*) Notice: Subject to any disclaimer, the term of this patent is extended or adjusted under 35 U.S.C. 154(b) by 136 days.

(21) Appl. No.: 15/322,890

(22) PCT Filed: Mar. 26, 2015

(86) PCT No.: PCT/KR2015/003013
§ 371 (c)(1),
(2) Date: Dec. 29, 2016

(87) PCT Pub. No.: WO2016/006794
PCT Pub. Date: Jan. 14, 2016

(65) Prior Publication Data
US 2017/0135586 A1    May 18, 2017

(30) Foreign Application Priority Data
Jul. 8, 2014  (KR) .................. 10-2014-0085395

(51) Int. Cl.
*A61B 5/00* (2006.01)
*A61B 5/0205* (2006.01)
(Continued)

(52) U.S. Cl.
CPC .......... *A61B 5/0205* (2013.01); *A61B 5/0077* (2013.01); *A61B 5/024* (2013.01);
(Continued)

(58) Field of Classification Search
CPC combination set(s) only.
See application file for complete search history.

(56) References Cited

U.S. PATENT DOCUMENTS

| 6,947,459 B2 * | 9/2005 | Kurtz ...................... H01S 5/36 |
| | | 348/E9.027 |
| 7,193,197 B2 * | 3/2007 | Sugiyama ......... H01L 27/14603 |
| | | 250/208.1 |

(Continued)

FOREIGN PATENT DOCUMENTS

| JP | 2012-038784 | 2/2012 |
| KR | 10-1000467 | 12/2010 |

(Continued)

OTHER PUBLICATIONS

International Search Report (with English Translation) and Written Opinion dated Jul. 13, 2015 issued in Application No. PCT/KR2015/003013.

*Primary Examiner* — Christopher A Flory
*Assistant Examiner* — Shirley X Jian
(74) *Attorney, Agent, or Firm* — KED & Associates, LLP (57) ABSTRACT The present invention provides a measuring apparatus comprising: a light source unit; and a sensor unit configured to sense a plurality of properties to be measured with respect to an object by using light emitted from the light source unit, wherein the sensor unit comprises: a first region configured to sense a first property to be measured among the plurality of properties to be measured by sensing the light within a first wavelength range; and a second region configured to sense a second property to be measured among the plurality of properties to be measured by sensing the light within a second wavelength range that is different from the first wavelength range.

14 Claims, 9 Drawing Sheets

(51) Int. Cl.
  *A61B 5/024* (2006.01)
  *A61B 5/1455* (2006.01)
  *A61B 5/145* (2006.01)

(52) U.S. Cl.
  CPC ........ *A61B 5/1455* (2013.01); *A61B 5/14532* (2013.01); *A61B 5/681* (2013.01); *A61B 5/742* (2013.01); *A61B 5/6826* (2013.01); *A61B 2562/046* (2013.01)

(56) References Cited

U.S. PATENT DOCUMENTS

| | | | | |
|---|---|---|---|---|
| 7,315,667 | B2* | 1/2008 | Schmidt | G01J 3/02 250/227.11 |
| 7,433,552 | B2* | 10/2008 | Kiesel | G01J 1/42 250/339.12 |
| 7,522,786 | B2* | 4/2009 | Kiesel | G01J 3/02 356/451 |
| 7,701,590 | B2* | 4/2010 | Kiesel | G01J 9/0246 356/454 |
| 7,718,948 | B2* | 5/2010 | Kiesel | G01J 3/02 250/208.2 |
| 8,373,860 | B2* | 2/2013 | Kiesel | G01N 21/05 356/417 |
| 8,629,981 | B2* | 1/2014 | Martini | G01N 21/05 356/28 |
| 8,805,465 | B2* | 8/2014 | Hodge | A61B 5/0002 600/310 |
| 9,146,230 | B2* | 9/2015 | Palti | G01N 33/5073 |
| 9,351,671 | B2* | 5/2016 | Ruchti | A61B 5/1455 |
| 9,351,672 | B2* | 5/2016 | Ruchti | A61B 5/1455 |
| 9,395,473 | B2* | 7/2016 | Choi | A61B 5/0075 |
| 9,433,385 | B2* | 9/2016 | Kasahara | A61B 5/1118 |
| 9,585,604 | B2* | 3/2017 | Ruchti | A61B 5/14532 |
| 9,615,798 | B2* | 4/2017 | Kasahara | A61B 5/1118 |
| 10,074,005 | B2* | 9/2018 | Chen | G06K 9/00087 |
| 2006/0209413 | A1* | 9/2006 | Kim | B82Y 20/00 359/577 |
| 2007/0146888 | A1* | 6/2007 | Schmidt | G01J 3/02 359/589 |
| 2008/0135739 | A1* | 6/2008 | Kim | G01J 3/02 250/226 |
| 2012/0129269 | A1* | 5/2012 | Choi | A61B 5/0075 436/164 |
| 2012/0136223 | A1* | 5/2012 | Hodge | A61B 5/0002 600/301 |
| 2013/0261413 | A1* | 10/2013 | Kawahara | A61B 5/14532 600/316 |
| 2014/0061486 | A1* | 3/2014 | Bao | G01J 3/0213 250/370.01 |
| 2015/0011850 | A1* | 1/2015 | Ruchti | A61B 5/14532 600/316 |
| 2015/0182150 | A1* | 7/2015 | Ikeda | A61B 5/1455 600/322 |
| 2015/0216458 | A1* | 8/2015 | Kasahara | A61B 5/742 600/316 |
| 2015/0216482 | A1* | 8/2015 | Kasahara | A61B 5/1118 600/301 |
| 2015/0216484 | A1* | 8/2015 | Kasahara | A61B 5/1118 600/301 |
| 2016/0058375 | A1* | 3/2016 | Rothkopf | G06F 1/1643 600/301 |
| 2016/0242682 | A1* | 8/2016 | Gulati | A61B 5/1455 |
| 2017/0055907 | A1* | 3/2017 | Altebaeumer | A61B 5/02416 |
| 2017/0188914 | A1* | 7/2017 | Dutta | A61B 5/14532 |
| 2017/0325721 | A1* | 11/2017 | Matsuda | A61B 5/117 |
| 2017/0357843 | A1* | 12/2017 | Chen | G06K 9/00087 |

FOREIGN PATENT DOCUMENTS

| KR | 2014/0024845 | 3/2014 |
|---|---|---|
| WO | WO 2012/049753 | 4/2012 |

* cited by examiner

MEASURING APPARATUS AND WEARABLE DEVICE COMPRISING SAME

CROSS-REFERENCE TO RELATED PATENT APPLICATIONS

This application is a U.S. National Stage Application under 35 U.S.C. § 371 of PCT Application No. PCT/KR2015/003013, filed Mar. 26, 2015, which claims priority to Korean Patent Application No. 10-2014-0085395, filed Jul. 8, 2014, whose entire disclosures are hereby incorporated by reference.

TECHNICAL FIELD

The present disclosure relates to a measuring apparatus for measuring a status of a target object, and a wearable device having the same.

BACKGROUND ART

X-ray radiography, ultrasonic imaging, computed tomography (CT) and the like, which are diagnostic imaging used in a clinical medicine are methods of imaging anatomical shape changes caused due to diseases. However, upon occurrence of a disease, biochemical changes and molecular genetic changes occur earlier than the biochemical changes.

Therefore, in recent time, a diagnosis paradigm is changing, for example, into monitoring of a quantity of motion, metabolism, biometric information and the like, for diagnosis of a disease in an imaging manner at the beginning of the disease.

Also, wearable devices are currently developed and studied in a direction of providing such devices with a monitoring function for the quantity of motion, the metabolism, the biometric information and the like. In this instance, if one information (object to be measured, property to be measured) is monitored for each sensor, there is a difficulty that a size of the wearable device increases in order to monitor various types of information. Therefore, a method of simultaneously monitoring various types of information through a sensor may be considered.

DISCLOSURE OF THE INVENTION

Therefore, an aspect of the detailed description is to provide a measuring apparatus for measuring a plurality of pieces of information through a small system.

Another aspect of the detailed description is to provide a wearable device for facilitating measurement of a status of a target object using reflected light.

To achieve these and other advantages and in accordance with the purpose of the present invention, as embodied and broadly described herein, there is provided a measuring apparatus, including a light source unit, and a sensor unit configured to sense a plurality of properties to be measured with respect to an object by using light emitted from the light source unit, wherein the sensor unit includes a first region configured to sense a first property to be measured among the plurality of properties to be measured by sensing the light within a first wavelength range, and a second region configured to sense a second property to be measured among the plurality of properties to be measured by sensing the light within a second wavelength range that is different from the first wavelength range.

In an embodiment disclosed herein, the sensor unit may include image sensing pixels forming an array, and the first region and the second region may correspond to regions dividing the image sensing pixels. The first region may be provided with a first filter and the second region is provided with a second filter configured to filter wavelengths within a different range from the first filter.

In an embodiment disclosed herein, the first filter may allow transmission of visible light therethrough to measure the first property to be measured in the first region, and the second filter may allow transmission of infrared light therethrough to measure the second property to be measured in the second region.

In an embodiment disclosed herein, each of the first and second properties to be measured may be one of a heart rate, an image of vein, calorie and blood sugar.

In an embodiment disclosed herein, the sensor unit may include a third region different from the first region and the second region, and the third region may be provided with a third filter configured to filter wavelengths within a different range from the first filter and the second filter. The third region may correspond to a region for measuring a third property to be measured different from the first and second properties to be measured.

In an embodiment disclosed herein, at least one of the first region and the second region may be configured such that wavelengths sensed therein are the same in one direction and increase in another direction perpendicular to the one direction. Filters arranged in at least one of the first region and the second region may filter different colors in the another direction. The first region and the second region may be arranged in the one direction.

In an embodiment disclosed herein, the sensor unit may include a sensor having a CMOS sensor or photodiode array, a plurality of filters disposed to overlap the sensor and transmitting therethrough light within the first wavelength range and the second wavelength range, respectively, and a lens disposed to cover the plurality of filters and configured to transfer the light to the sensor.

In an embodiment disclosed herein, the lens may include a plurality of unit lenses arranged on the same plane.

In an embodiment disclosed herein, the sensor unit may include barrier walls each interposed between adjacent pixels of the sensor.

Also, the present invention provides a wearable device wearable on a wrist, the device including a main body having a display unit, a band connected to the main body to surround the wrist such that the main body is worn on the wrist, a measuring apparatus provided with a light source unit to output light, and a sensor unit to sense reflected light reflected from the wrist to measure a plurality of properties to be measured, the measuring apparatus disposed on the band, and a controller to control the measuring apparatus and the display unit to output results measured by the measuring apparatus on the display unit.

Advantageous Effect

According to the measuring apparatus according to the present invention having such configuration, a plurality of biometric information (heart rate, blood sugars, calories, etc.) can be monitored on a wearable device. Also, the measuring apparatus can serve as a sensor for authenticating biometric information such as finger vein.

According to the present invention, a plurality of biometric information can be measured by using a widely-used CMOS sensor. Therefore, a micro measuring apparatus or a measuring apparatus capable of measuring various types of biometric information can be implemented using a single chip sensor.

MODES FOR CARRYING OUT THE PREFERRED EMBODIMENTS

Description will now be given in detail of a measuring apparatus and a wearable device having the same according to exemplary embodiments disclosed herein, with reference to the accompanying drawings. For the sake of brief description with reference to the drawings, the same or equivalent components may be provided with the same or similar reference numbers, and description thereof will not be repeated.

Figure 1:
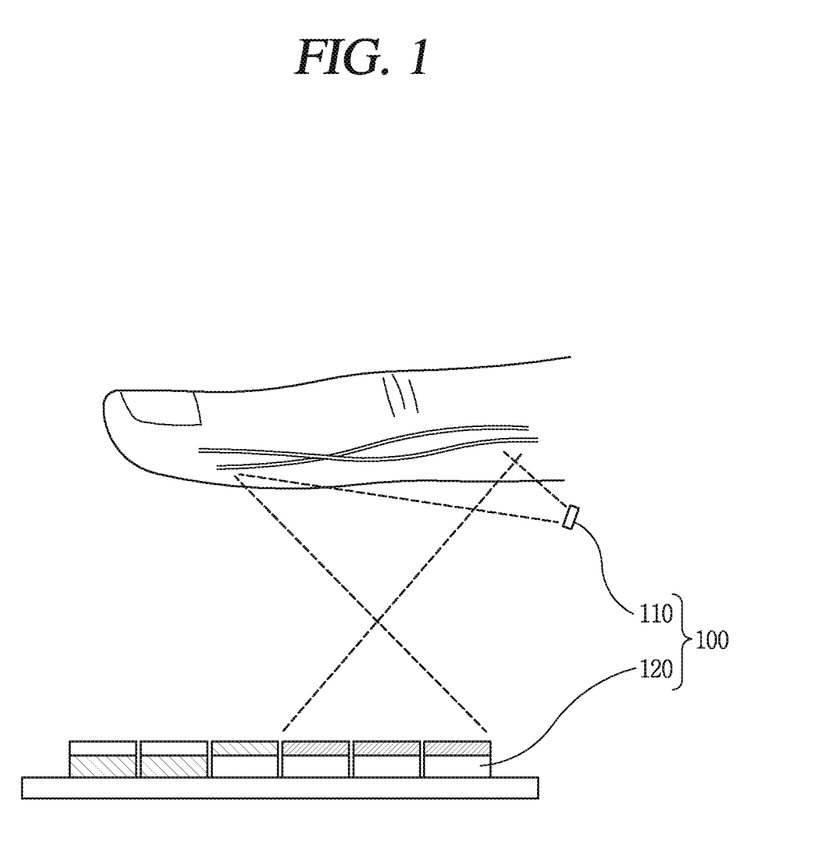
FIG. 1 is a conceptual view illustrating a measuring method in accordance with one embodiment of the present invention.

FIG. 1 is a conceptual view illustrating a measuring method in accordance with one embodiment of the present invention.

As illustrated, a target object enters in one direction and is placed at a specific position of a measuring apparatus 100. The object may be a part of a human body (a finger in this embodiment). However, the present invention may not be limited to this, and the object may be another part of the human body, for example, a wrist, an elbow, a shoulder, a foot, an ankle, a knee and the like.

The measuring apparatus 100 is configured to output light within a specific wavelength range (or electromagnetic wave within a specific wavelength range) toward the object, and detect (sense) light reflected from the object (hereinafter, referred to as reflected light). However, the present invention may not be necessarily limited to this. The measuring apparatus 100 may alternatively be configured to detect light transmitted through the object (hereinafter, referred to as transmitted light) or detect both of the reflected light and the transmitted light.

The output light within the specific wavelength range may be in the wavelength range of 530 nm to 1100 nm. The measuring apparatus 100 may divide the wavelength range into a plurality of wavelength ranges, and detect and treat the reflected light within the plurality of wavelength ranges. However, the present invention may not be necessarily limited to this, but the wavelength range may be another wavelength range.

The measuring apparatus 100 includes a light source unit 110 and a sensor unit 120.

The light source unit 110 may be configured to output light within the specific wavelength range, and controlled by a controller.

Referring to this drawing, the light source unit 110 of the measuring apparatus 100 may output light toward the object or emit light toward the object using an intermediate medium. Also, the light source unit 110 may output light within a broadband. As one example, the light source unit 110 may include a light-emitting diode (LED) and the like as a light source. However, the present invention may not be necessarily limited to this, but may alternatively include various types of light sources, for example, using a laser diode that outputs near-infrared laser beams within a near-infrared wavelength range, and the like.

The sensor unit 120 detects the reflected light, and the controller measures a state of the object by comparing the reflected light with preset data.

Referring to the drawing, the sensor unit 120 is arranged with being spaced apart from the light source unit 110, and senses light that is incident on a specific point of the object and then reflected or transmitted by or through the object. In this instance, the sensor unit 120 senses light, which is emitted from the light source unit and reflected by the object, on the region basis, in order to sense a plurality of properties to be measured with respect to the object. In this instance, the properties to be measured may be, for example, a heart beat, a vein image, calorie, blood sugar and the like.

According to the measuring method, diagnosis for the plurality of properties to be measured may be made in terms of precaution and management. Hereinafter, description will be given of a detailed structure of a measuring apparatus, which can more specify the measuring method, and be commercialized even with employing the measuring method.

Figure 2:
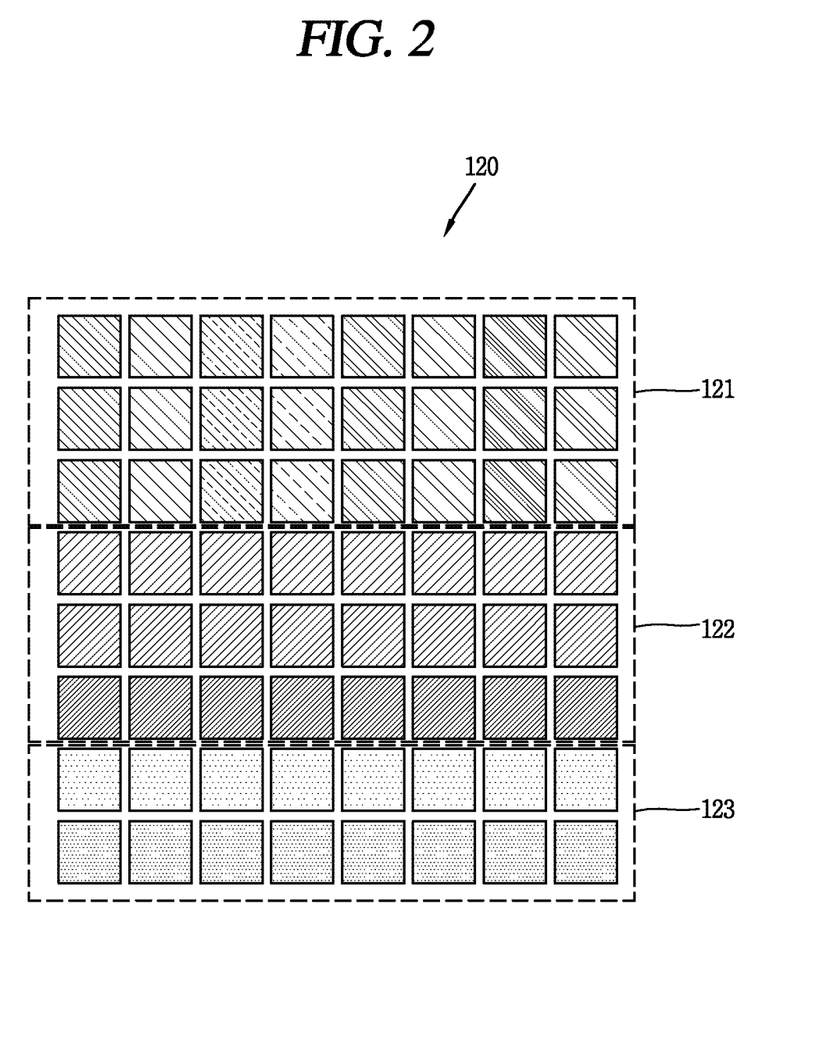
FIG. 2 is a conceptual view illustrating one embodiment of a measuring apparatus according to the present invention.
Figure 3A:
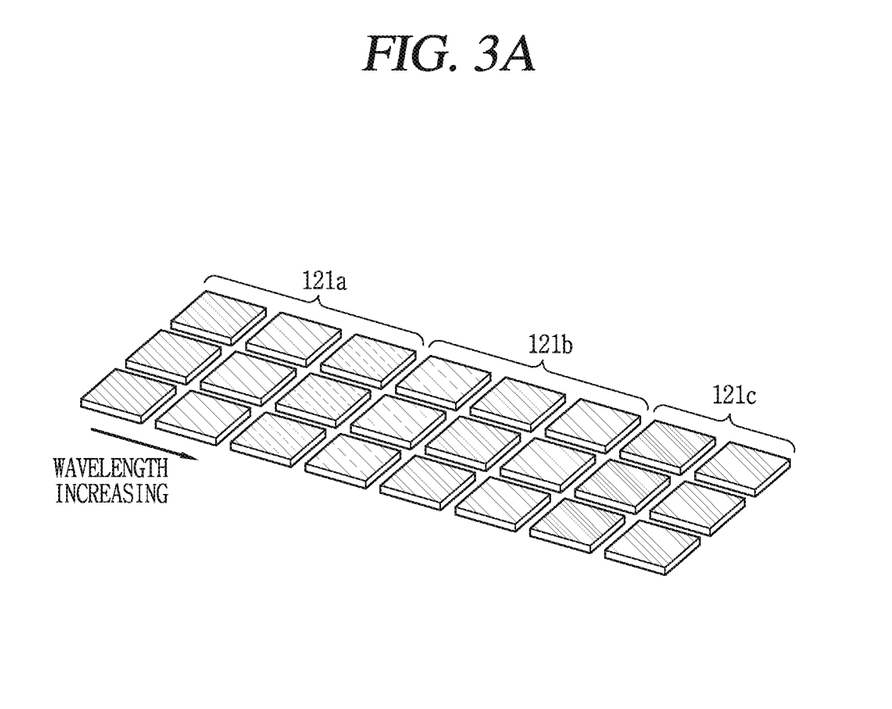
FIGS. 3A and 3B are an enlarged view and an operation conceptual view of a first area of the measuring apparatus of FIG. 2.
Figure 3B:
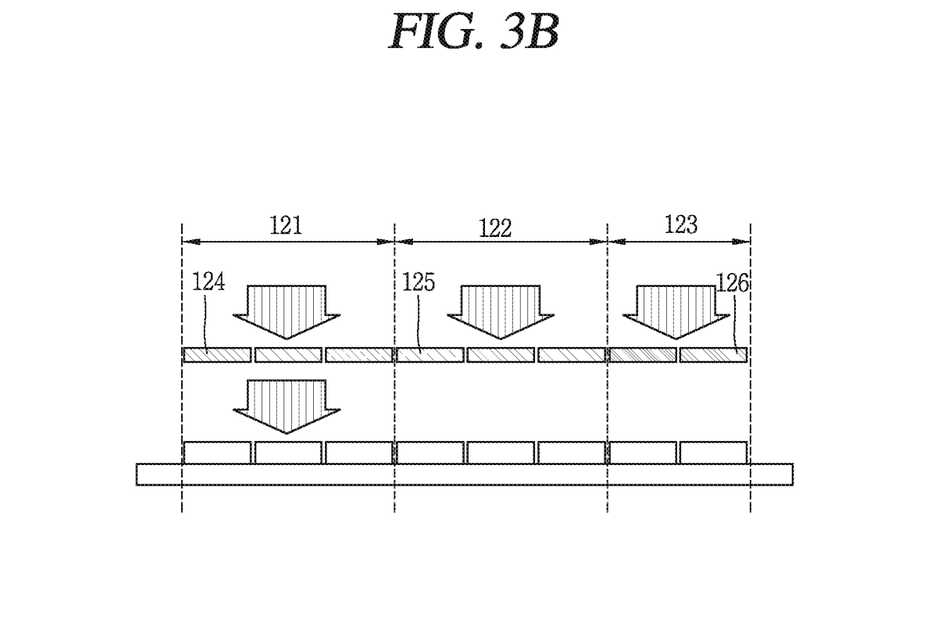
Figure 4A:
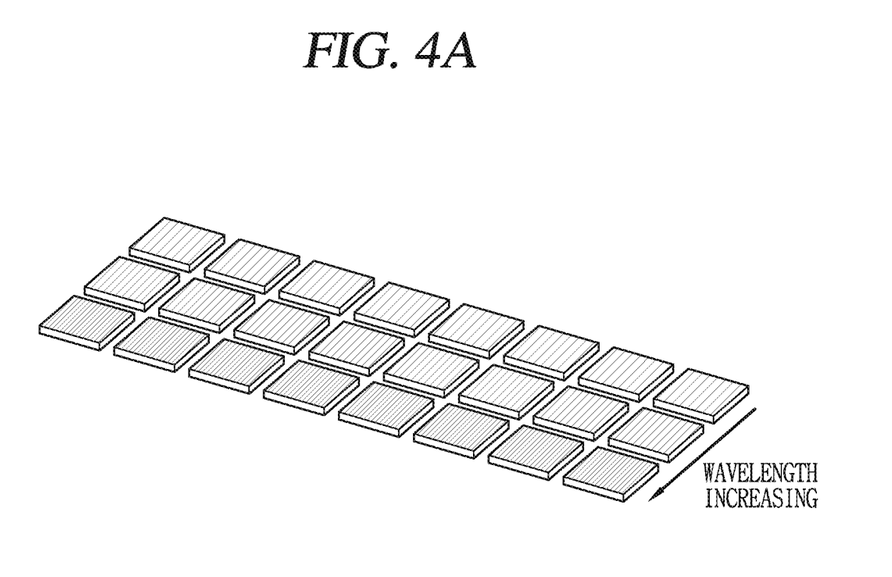
FIGS. 4A and 4B are an enlarged view and an operation conceptual view of a second area of the measuring apparatus of FIG. 2.
Figure 4B:
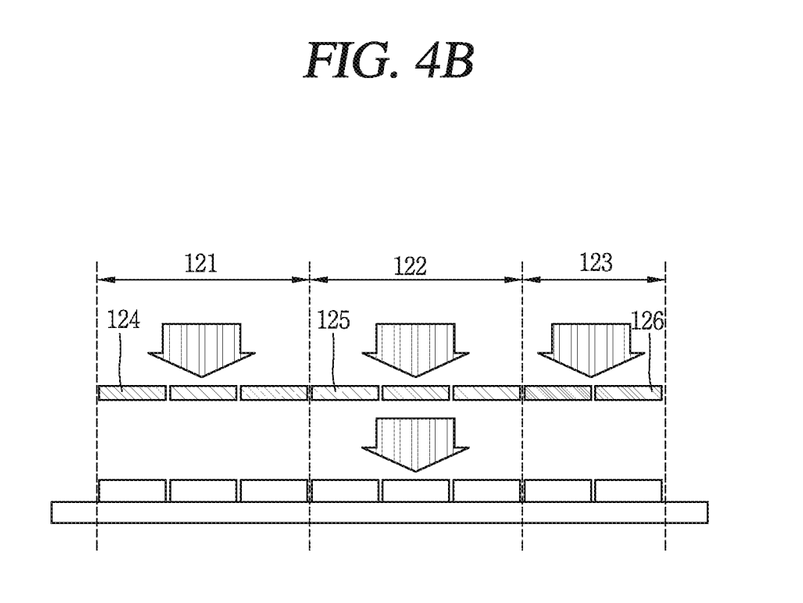
Figure 5:
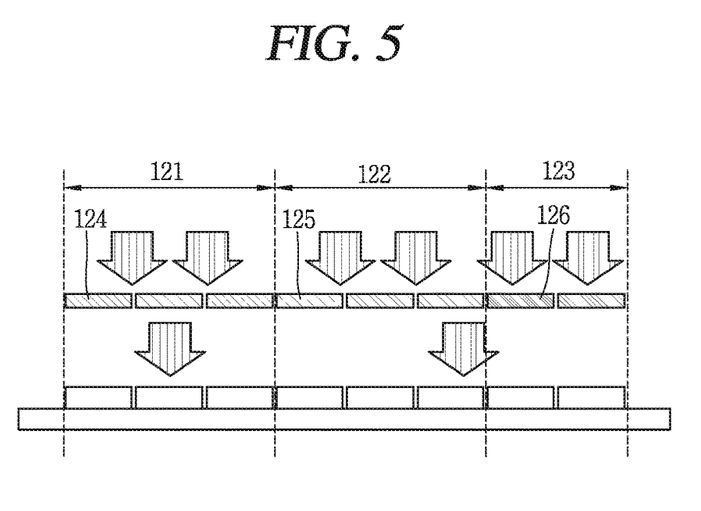
FIG. 5 is an operation conceptual view related to a third area of the measuring apparatus of FIG. 2.

FIG. 2 is a conceptual view illustrating one embodiment of a measuring apparatus according to the present invention, FIGS. 3A and 3B are an enlarged view and an operation conceptual view of a first area of the measuring apparatus of FIG. 2, FIGS. 4A and 4B are an enlarged view and an operation conceptual view of a second area of the measuring apparatus of FIG. 2, and FIG. 5 is an operation conceptual view related to a third area of the measuring apparatus of FIG. 2.

Referring to those drawings, the sensor unit 120 includes image sensing pixels forming an array. As a related example, the sensor unit 120 may include a CMOS sensor array or a photodiode array. Also, the sensor unit 120 is divided into a plurality of regions. In this instance, the plurality of regions may be defined by filters provided therein. First, the plurality of regions include a first region 121 and a second region 122. Here, the first region 121 and the second region 122 may correspond to regions dividing the image sensing pixels. As a related example, each region may include a different group of pixels of a CMOS sensor.

The first region 121 senses reflected light, which is output from the light source unit and reflected from an object, within a first wavelength range. Also, the second region 122 sense the reflected light within a second wavelength range different from the first wavelength range. In this instance, the first wavelength range, for example, may be a range corresponding to visible light (380 to 750 nm), and the second wavelength range, for example, may be a range corresponding to near infrared light (0.75 to 1.3 μm).

As such, in order to sense the visible light for each different wavelength range, a first filter 124 may be disposed in the first region 121 and a second filter 125 which filters a wavelength within a different range from the first filer 124 may be disposed in the second region 122. As the wavelength ranges filtered are different, the first region 122 senses a first property to be measured of a plurality of properties to be measured, and the second region 122 senses a second property to be measured of the plurality of properties to be measured. In this instance, each of the first property to be measured and the second property to be measured may be one of a heart beat, a vein image, calorie and blood sugar.

According to the above description, the first filter 124 may be configured to transmit visible light therethrough to measure the first property to be measured within the first region 121, and the second filter 125 may be configured to transmit infrared light therethrough to measure the second property to be measured within the second region 122. As a more detailed example, the first filter 124 may transmit therethrough only light within a range of 530 to 750 nm and the second filter 125 may transmit therethrough only light within a range of 750 to 950 nm. Accordingly, the first region 121 may be a region for sensing the heart beat, and the second region 122 may be a region for sensing the image of finger vein.

Referring to FIGS. 2, 3A and 3B, the first region 121 is a region for applying a heart rate sensor (plethysmography (PPG) sensor). Considering light that is absorbed by a sensor due to absorption, scattering and reflection of light with respect to skin and blood vessel within a wrist, a light source can select a central wavelength in various ranges between 570 and 750 nm.

In more detail, the first region 121 may be configured in a manner that wavelengths sensed are the same in one direction and increase in another direction perpendicular to the one direction. In this instance, the first region 121 and the second region 122 are arranged in the one direction. For example, the filter disposed in the first region 121 filters a different color in the another direction. This filter may include unit filters which may allow transmission of only a narrow wavelength spectrum ranging from several nanometers (nm) to tens of nanometers (nm) by dividing consecutive wavelengths. The unit filters are arranged on each pixel or pixel group of the CMOS sensor.

For example, the first region 121 may include a first sub region 121a and a second sub region 121b. The first sub region 121a has a wavelength range of 530 to 590 nm to filter green light, and the second sub region 121b may have a wavelength of 590 to 680 nm to filter red light. In addition, the first region 121 may further include a third sub region 121c having a wavelength range of 680 to 750 nm to filter near infrared light. With the structure, light within the wavelength range of 530 to 770 nm can be used, and this light within the range corresponds to a measurement range of a heart rate sensor.

The filter can utilize nano-patterned unit filters using a surface plasmonic effect or quantum dots that vary absorption wavelength bands according to a no-particle size due to a nano-sized quantum confinement effect. Here, the surface plasmonic effect refers to an effect that electric fields and plasmons of light in a visible or infrared band absorb light while paired with each other, so as to have clear colors. Here, the plasmons are quasi-particles that electrons located on a surface of a metal nano-particle resonantly oscillate according to a wavelength of specific light when the specific light is incident on a metallic nano structure formed in a nano size. In this instance, the wavelength range in which the electrons resonate can be adjusted by a shape of a nano structure, a refractive index of a material forming the nano structure, and the like.

Referring to FIGS. 4A and 4B, the second region 122 may be a region for sensing an image of finger vein or palm vein. To this end, a CMOS sensor and a near-infrared light source (light source with central wavelength in the range of 770 nm to 950 nm) are utilized. The second region 122 is formed for authenticating biometric information through transmitted or reflected imaging of a vein of a finger or palm.

The near-infrared wavelengths may be set within the range of 770 to 950 nm by considering a transmission depth of a skin and a hemoglobin absorption spectrum. In this instance, for imaging the reflected or transmitted vein, wavelength filters of the CMOS sensor and the photodiode are combined with each other so as to filter and sense light within the wavelength region of 770 to 950 nm.

In more detail, the second region 122, unlike the first region 121, may be configured such that the wavelengths sensed are the same in another direction and increase in one direction perpendicular to the another direction. Accordingly, the increase in the sensed wavelengths is made in a direction perpendicular to the first region. Here, the second filter 125 disposed in the second region 122 may include unit filters that allow transmission of only a narrow wavelength spectrum ranging from several nanometers (nm) to tens of nanometers (nm) by dividing consecutive wavelengths. The unit filters are arranged on each pixel or pixel group of the CMOS sensor. A method of forming the unit filters may be the same as that used for the first region.

With the structure, the measuring apparatus 100 (see FIG. 1) can use light within the range of 770 to 950 nm in the second region. This range of light corresponds to a measurement range of a sensor for authenticating biometric information, such as an image of finger vein or palm vein.

Referring to FIG. 5, the sensor unit 120 includes a third region 123 different from the first region 121 and the second region 122. A third filter 126 for filtering a wavelength within a different range from those of the first filter 124 and the second filter 125 may be disposed in the third region 123. In this instance, the third region 123 corresponds to a region for measuring a third property to be measured different from the first property to be measured and the second property to be measured. In more detail, the first property to be measured may be a heart beat, the second property to be measured may be a vein image, and the third property to be measured may be calorie, blood sugar or the like.

In this instance, the third region 123 may be configured such that wavelengths sensed are the same in one direction and increase in another direction perpendicular to the one direction. This filter may include unit filters that allow transmission of only a narrow wavelength spectrum ranging from several nanometers (nm) to tens of nanometers (nm) by dividing consecutive wavelengths. The unit filters are arranged on each pixel or pixel group of the CMOS sensor. A method of forming the unit filters may be the same as that used for the first region.

Also, the third filter 126 transmits therethrough light within a range of 950 to 1100 nm, which allows the measuring apparatus 100 to measure and monitor blood sugar within a human body. For example, since light is absorbed at a specific wavelength due to sugar compositions within a vessel in a wrist, a function of monitoring changes in blood sugars and calories by analyzing changes in transmitted and reflected light spectrums is realized. In addition, since the first region 121 and the second region 122 are combined with the third region 123, light can be sensed within the range of 530 to 1100 nm. Therefore, the light spectrum can be analyzed within the range of 530 to 1100 nm.

Each of those regions may vary into various forms, and variations of those regions will now be described with reference to the accompanying drawings.

Figure 6A:
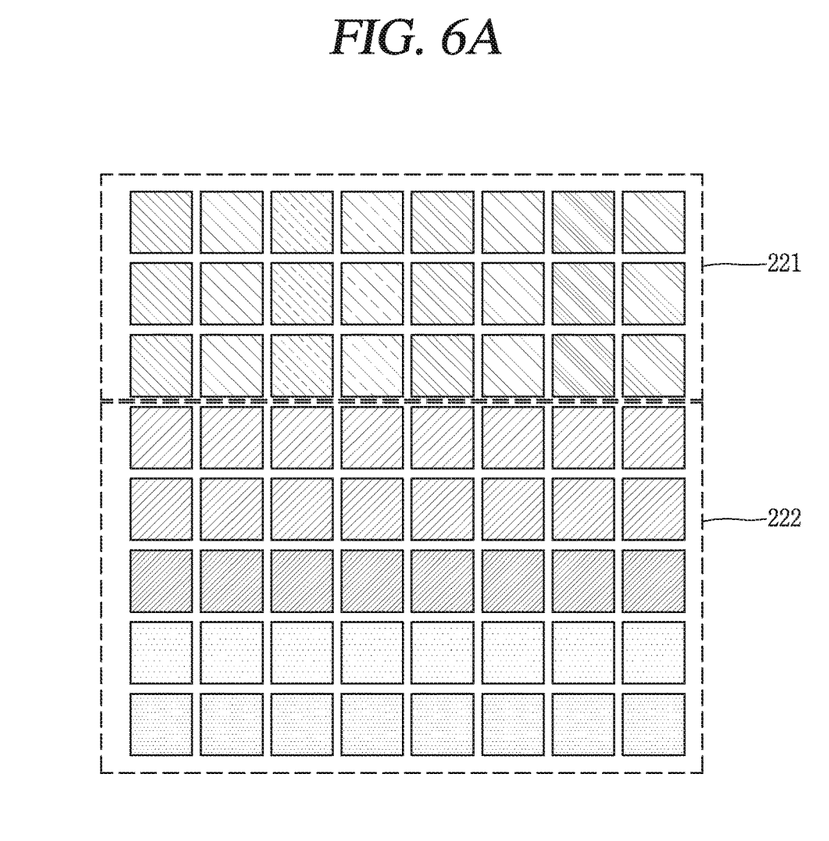
FIGS. 6A and 6B are conceptual views illustrating another embodiment of a measuring apparatus according to the present invention.
Figure 6B:
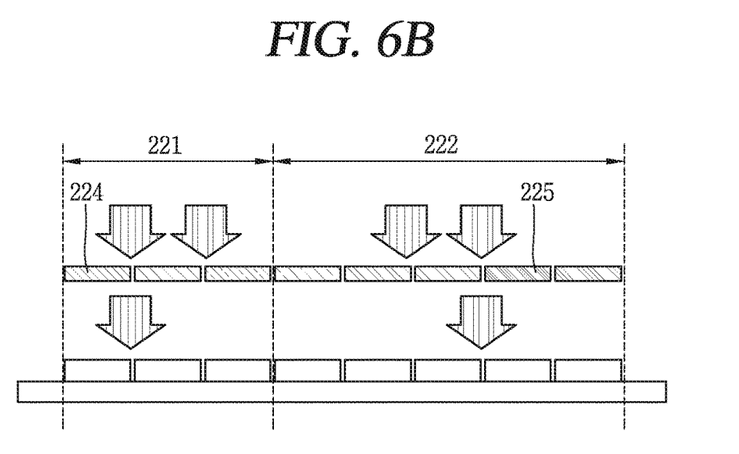

FIGS. 6A and 6B are conceptual views illustrating another embodiment of a measuring apparatus according to the present invention.

As illustrated in those drawings, a sensor unit 220 includes a first region 221 and a second region 222. In more detail, the sensor unit 220 may merely include the first region 221 and the second region 222 without a third region.

Similar to those illustrated in the first embodiment described with reference to FIGS. 2 to 5, the first region 221 senses light within a first wavelength range, and the second region 22 senses the light within a second wavelength range different from the first wavelength range. In this instance, the first wavelength range, for example, may be a range corresponding to visible light (360 to 750 nm), and the second wavelength range may be a range corresponding to near-infrared light (0.75 to 1.3 μm).

As a more detailed example, a first filter 224 of the first region 221 may be configured to transmit therethrough light in the range of 530 to 750 nm, and a second filter 225 may be configured to transmit therethrough light in the range of 750 to 1100 nm. Accordingly, the first region 221 may be a region sensing a heart beat, and the second region 222 may be a region sensing an image of finger vein. In this instance, a combined region of the first and second regions is defined as a region for measuring calories or blood sugars.

In more detail, the first filter 224 filters the same wavelength range as the first filter of the first embodiment, but the second filter 225 filters a different wavelength range from the second filter of the first embodiment. In this instance, the second filter 225 may have the same structure as that illustrated in the first embodiment, except for the wavelength range. Therefore, the first region 121 may be configured such that wavelengths sensed are the same in one direction and increase in another direction perpendicular to the one direction. Here, the first region 121 and the second region 122 are arranged in the one direction. For example, the filter disposed in the first region 121 filters a different color of light in the another direction. Therefore, the second region 222 may be configured such that the sensed wavelengths increase in a direction perpendicular to the increasing direction of the wavelengths in the first region 221.

Figure 7A:
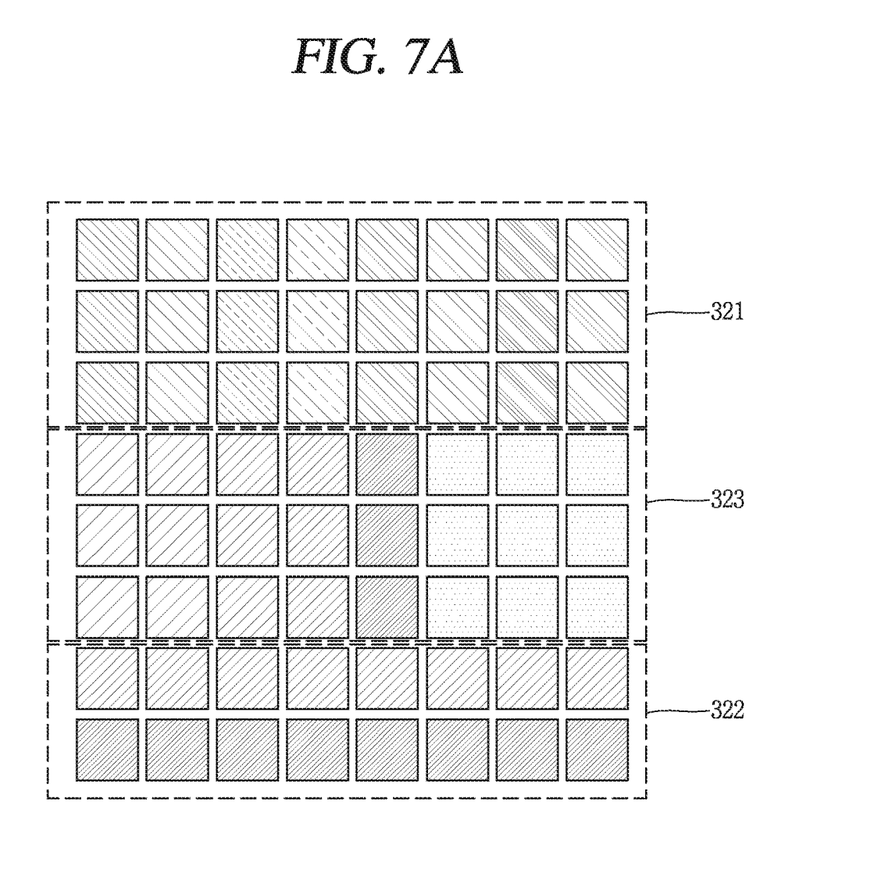
FIGS. 7A and 7B are conceptual views illustrating another embodiment of a measuring apparatus according to the present invention.
Figure 7B:
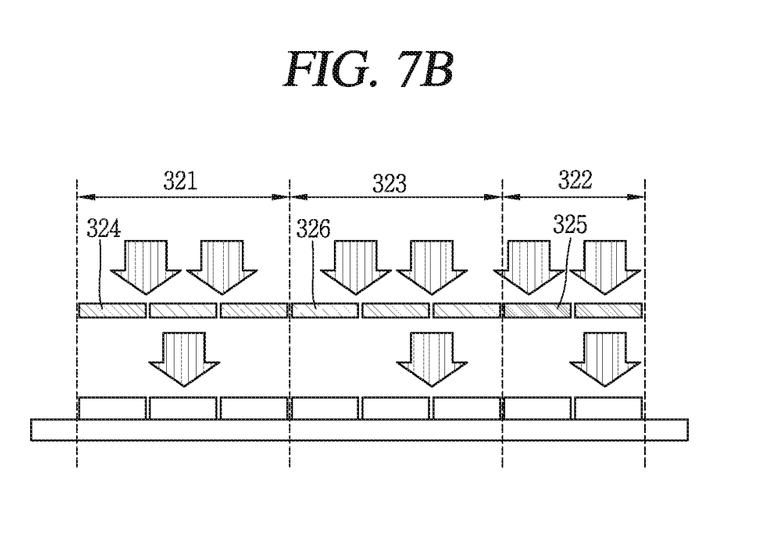

FIGS. 7A and 7B are conceptual views illustrating another embodiment of a measuring apparatus according to the present invention.

Referring to those drawings, a sensor unit 320 includes a first region 321, a second region 322 and a third region 323. The third region 323 is interposed between the first region 321 and the second region 322. In this instance, the first region 321 is a region for sensing a heart beat, and the second region 322 is a region for sensing an image of finger vein. Structures of those are the same as those illustrated with reference to FIGS. 2 to 5.

In this embodiment, the third region 323 is a region for sensing calories or blood sugars, and a third filter 326 disposed in the third region 323 may be configured to transmit therethrough only light in the range of 750 to 1100 nm. With this structure, the first region 321 and the third region 323 may be combined with each other so as to serve as a region for sensing calories or blood sugars.

Also, the third filter 326 of the third region 323 may be configured, similar to the first filter 324 of the first region 321, such that wavelengths sensed are the same in one direction and increase in another direction perpendicular to the one direction. On the other hand, the second filter 325 of the second region 322 may be configured such that sensed wavelengths are the same in the another direction and increase in the one direction. This filter, similar to that of the previous embodiment, may include unit filters which may allow transmission of only a narrow wavelength spectrum ranging from several nanometers (nm) to tens of nanometers (nm) by dividing consecutive wavelengths. The unit filters are arranged on each pixel or pixel group of the CMOS sensor.

The foregoing description has been given of the structure and method for measuring a different property to be measured in each region of a sensor unit. This may allow for measuring a plurality of biometric information using a single CMOS sensor or photodiode.

As such, an optical system is required for transferring optical information to each pixel of the CMOS sensor or photodiode. Hereinafter, a structure of a sensor unit having the optical system will be described in more detail.

Figure 8A:
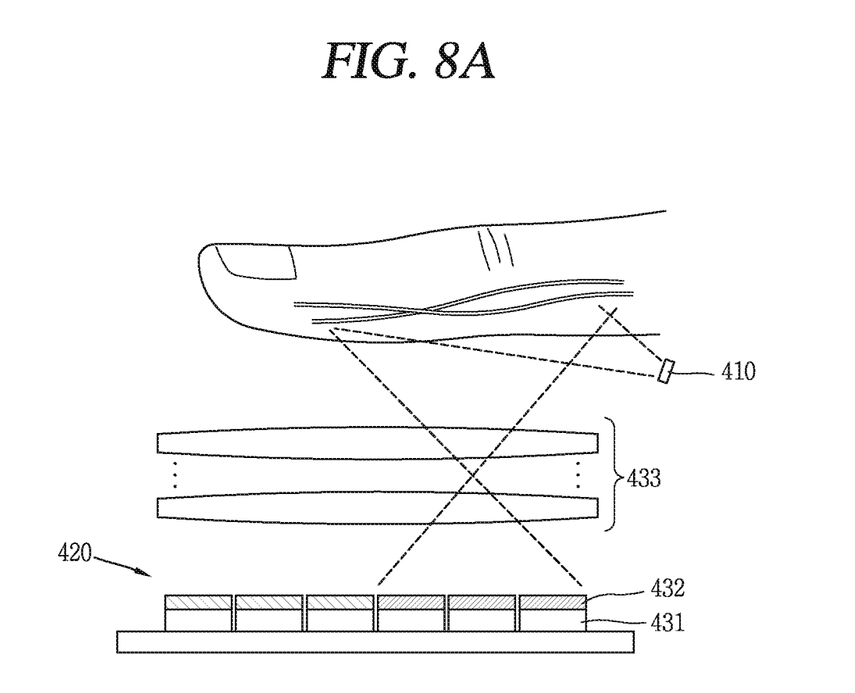
FIGS. 8A, 8B and 8C are conceptual views illustrating structures of a sensor unit according to the present invention, respectively.
Figure 8B:
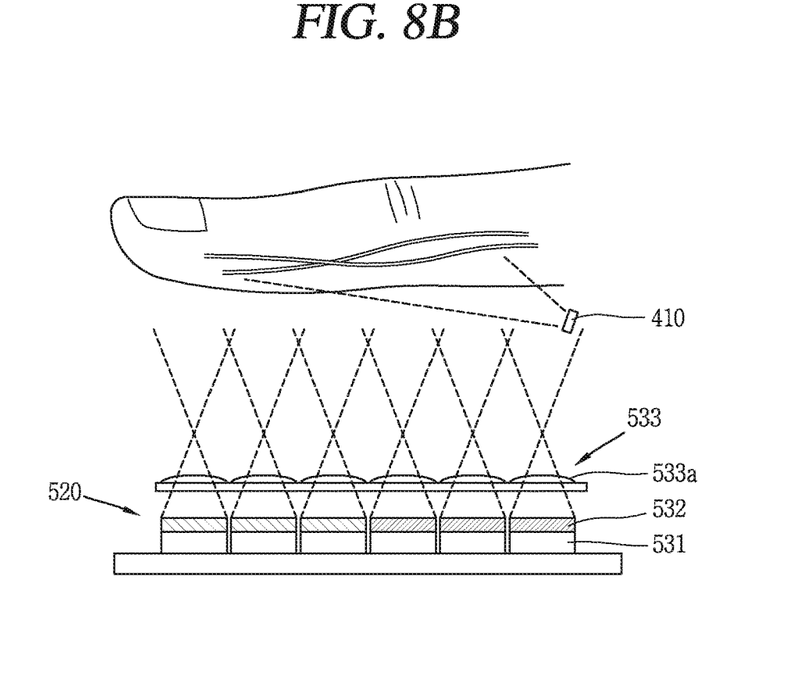
Figure 8C:
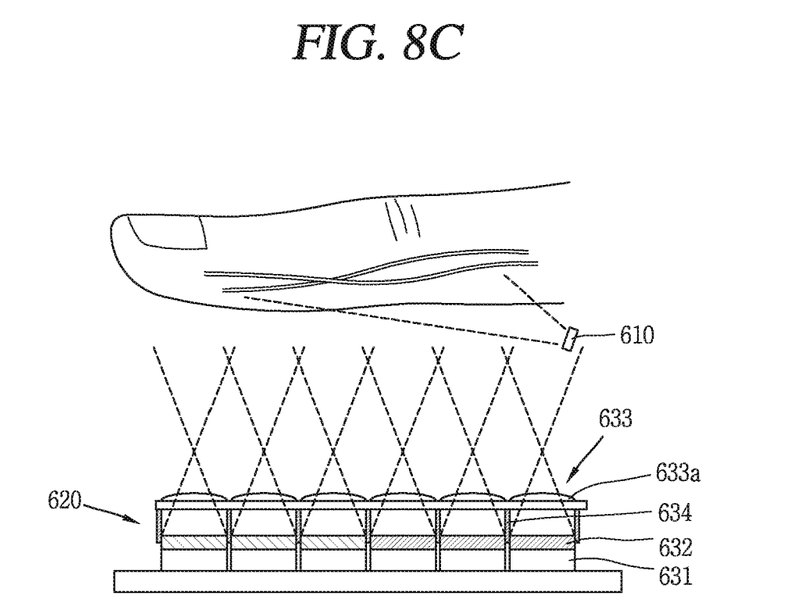

FIGS. 8A, 8B and 8C are conceptual views illustrating structures of sensor units according to the present invention, respectively.

Referring to FIG. 8A, a sensor unit 420 includes a sensor 432, a plurality of filters 432 and a lens 433.

The sensor 431 may include the CMOS sensor or photodiode array described in the previous embodiment. Also, the plurality of filters 432, as illustrated in the previous embodiment, overlap the sensor and transmit light within the first wavelength range and the second wavelength range, respectively.

The lens 433 is provided to cover the plurality of filters 432 and transfers light, which is output from a light source unit 410 and scattered, transmitted or reflected by an object, to the sensor. As an example, the lens 433 may be a multi-lens with a plurality of lenses. That is, bulk lenses are arranged in an output direction of light to optically image a region of interest in an one sight manner. In this instance, the number of sensor arrays corresponds to resolution (or number of pixels) of a commercial CMOS sensor.

As another example, referring to FIG. 8B, the lens 533 may include a plurality of unit lenses 533a arranged on the same plane. That is, a method of dividing a region of interest using a micro lens array may be used. In this instance, a thickness of the measuring apparatus can be minimized. However, the present invention may not be necessarily limited to this. The lens 533 may be a bundle of a plurality of optical fibers (not illustrated) arranged to cover the sensor unit 520. The plurality of optical fibers can transfer an image, which is generated by light reflected, transmitted and scattered by the object, in a manner of dividing the image into a plurality of pieces, and thus may be referred to as an optical transfer unit. As a related example, the plurality of optical fibers may be fiber optic face plates (FOFPs). Also, in this instance, a design condition of a micro lens array and a pixel pitch or size relation may be set from an imaging region (region of interest) of the sensor unit for vein authentication, other than a region of a PPG sensor and a blood sugar sensor.

As another example, referring to FIG. 8C, a sensor unit 620 may include barrier walls 634 interposed between adjacent pixels of the sensor. As illustrated, a lens 633 may include a plurality of unit lenses 633a arranged on the same plane. That is, a method of dividing a region of interest using a micro lens array may be used. The barrier wall 634 may be disposed between the lens 633 and the filter 632, and accordingly the sensor unit may simultaneously have a reflection characteristic and high contrast.

The aforementioned measuring apparatus may also be mounted in a wearable device. The wearable device may be a smart watch, a smart glass, a head mounted display (HMD), a smart band and the like. Hereinafter, this structure will be described in more detail.

Figure 9A:
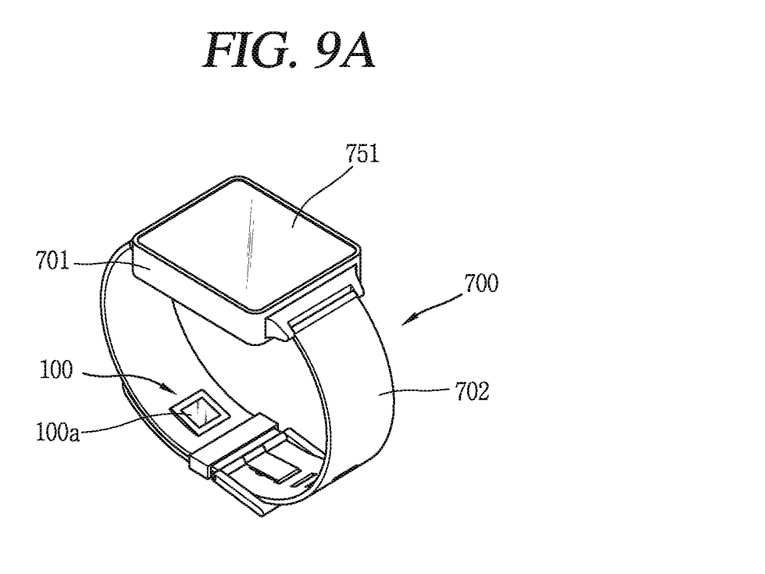
FIGS. 9A and 9B are a perspective view and a partial exploded view each illustrating a wearable device having the measuring apparatus according to the present invention.
Figure 9B:
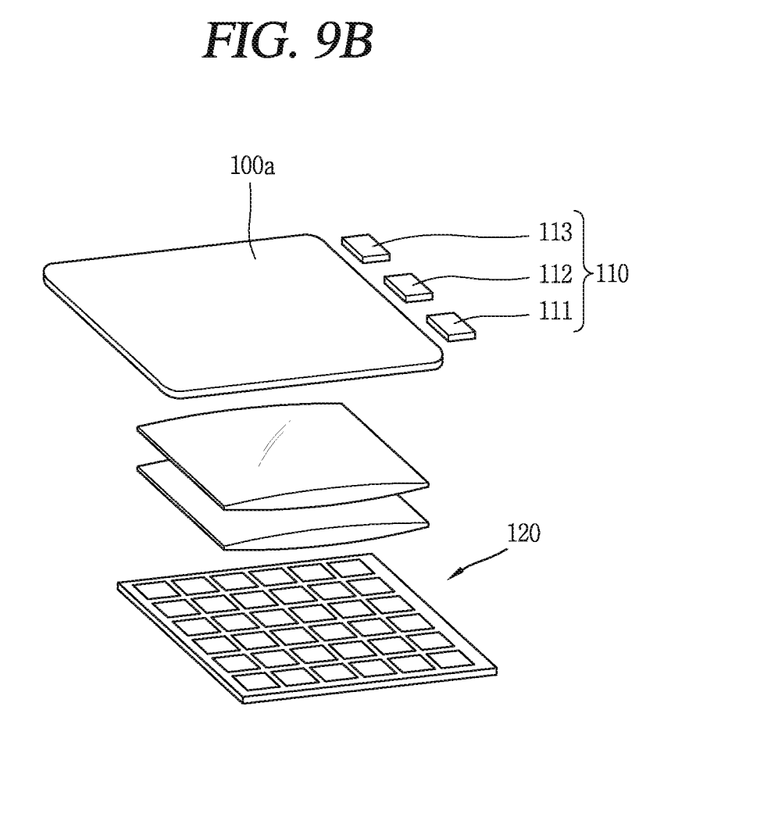

FIGS. 9A and 9B are a perspective view and a partial exploded view each illustrating a wearable device having the measuring apparatus according to the present invention.

As illustrated in those drawings, a wearable device 700 according to this embodiment includes a main body 701 having a display unit 751, and a band 702 connected to the main body 701 to be wearable on a wrist.

The main body 701 includes a case defining appearance. As illustrated, the case may include first and second cases defining an inner space accommodating various electronic components therein. However, the present invention may not be limited to this. Alternatively, one case may be configured to define the inner space, so as to implement a device 700 with a uni-body.

The display unit 751 may be disposed on a front surface of the main body 701 to output information, and a touch sensor may be provided on the display unit 751 to implement a touch screen.

The band 702 is worn on a user's wrist and may be made of a flexible material for facilitating wearing of the device. Also, the band 702 may be detachable from the main body 701 so as to be replaceable with various types of bands according to a user's preference.

Referring to FIG. 9A, the measuring apparatus 100 described with reference to FIGS. 1 to 8C may be disposed on the band. Referring to FIG. 9B, the measuring apparatus is provided with a window 100a arranged on an inner surface of the band, and the sensor unit 120 illustrated in the previous embodiment is arranged to be covered by the window 100a. In this instance, the light source unit 110 may be disposed adjacent to one side of the window to output light with a broadband. In this instance, light within a wavelength range for measuring heart beats or blood sugars may be output toward a wrist in a direction perpendicular to the window 100a, and light for measuring an image of vein may be output in a direction horizontal to the window 100a to be scattered at the window 100a. In more detail, a first light source 111 outputting light within a wavelength range of 530 to 750 nm and a third light source 113 outputting light within a wavelength range of 950 to 110 nm are arranged to output in a perpendicular direction to a second light source 112 outputting light within a wavelength range of 750 to 950 nm.

In this instance, a controller controls the measuring apparatus and the display unit to output measurement results of the measuring apparatus on the display unit. For example, graphic user interfaces associated with a heart beat, an authentication of finger vein and calorie checking may be sequentially output on the display unit. For the heart beat, a heart rate per minute or heart rate waveform may be output on the display unit. For the blood sugar or calorie, data notifying the blood sugars or calories may be output on the display unit. This may allow a user to monitor a plurality of biometric information (heart rate, blood sugars, calories, etc.)

The present invention may not be limited to the configuration and method of the embodiments associated with the measuring apparatus, but alternatively be applied even to measurement for other portions of a human body or commercial measurement. For example, the present invention can be applied to measurement of other lesions, such as carpel tunnel syndrome, measurement of a spoiled degree of a plant, and the like.

Also, all or part of each of the embodiments may selectively be combined to make various modifications and variations.

The invention claimed is:

1. A measuring apparatus, comprising:
a light source; and
a sensor configured to sense a plurality of properties to be measured with respect to an object by using light emitted from the light source,
wherein the sensor includes:
a first region configured to sense a first property to be measured among the plurality of properties by sensing light within a first wavelength range; and
a second region configured to sense a second property to be measured among the plurality of properties by sensing light within a second wavelength range that is different from the first wavelength range,
wherein the sensor includes image sensing pixels forming an array, and the first region and the second region are included in regions dividing the array of the image sensing pixels,
wherein first image sensing pixels within the first region sense same wavelengths in a first direction and incrementally increasing wavelengths in a second direction that is perpendicular to the first direction, and
wherein second image sensing pixels within the second region sense incrementally increasing wavelengths in the first direction and same wavelengths in the second direction.

2. The apparatus of claim 1, wherein the first region is provided with a first filter, and the second region is provided with a second filter configured to filter wavelengths within a different range from the first filter.

3. The apparatus of claim 2, wherein the first filter allows transmission of visible light there through to measure the first property to be measured in the first region, and the second filter allows transmission of infrared light therethrough to measure the second property to be measured in the second region.

4. The apparatus of claim 3, wherein each of the first and second properties to be measured relates to one of a heart rate, an image of vein, calories, or blood sugar.

5. The apparatus of claim 3, wherein the sensor further includes a third region different from the first region and the second region, and the third region is provided with a third filter configured to filter wavelengths within a different range from the first filter and the second filter.

6. The apparatus of claim 5, wherein the third region corresponds to a region to measure a third property to be measured that is different from the first and second properties.

7. The apparatus of claim 1, wherein filters provided in at least one of the first region or the second region filter different colors in the second direction.

8. The apparatus of claim 1, wherein the first region and the second region are arranged in the first direction.

9. The apparatus of claim 1, wherein the sensor includes:
at least one of a CMOS sensor or photodiode array;
a plurality of filters disposed to overlap the sensor and configured to transmit there through light within the first wavelength range and the second wavelength range, respectively; and a lens disposed to cover the plurality of filters and configured to transfer the light to the CMOS sensor or the photodiode array.

10. The apparatus of claim 9, wherein the lens includes a plurality of unit lenses arranged on a same plane.

11. The apparatus of claim 9, wherein the sensor further includes barrier walls that are each interposed between adjacent pixels of the sensor.

12. A device wearable on a wrist of a user, the device comprising:
- a main body having a display;
- a band connected to the main body to surround the wrist such that the main body is provided on the wrist,
- a measuring apparatus including a light source to output light, and a sensor to sense light reflected from the wrist to measure a plurality of properties, the measuring apparatus being provided on the band; and
- a controller to control the measuring apparatus and the display such that results measured by the measuring apparatus are outputted on the display,
- wherein the sensor includes:
    - a first region to sense a first property to be measured based on sensing light within a first wavelength range; and
    - a second region to sense a second property to be measured based on sensing light within a second wavelength range that is different from the first wavelength range,
- wherein the sensor includes image sensing pixels forming an array, and the first region and the second region are included in regions dividing the array of the image sensing pixels,
- wherein first image sensing pixels within the first region sense same wavelengths in a first direction and incrementally increasing wavelengths in a second direction that is perpendicular to the first direction, and
- wherein second image sensing pixels within the second region sense incrementally increasing wavelengths in the first direction and same wavelengths in the second direction.

13. The wearable device of claim 12, wherein the first region is provided with a first filter and the second region is provided with a second filter that filters wavelengths within a different range from the first filter.

14. The wearable device of claim 13, wherein the first filter allows transmission of visible light therethrough to measure the first property to be measured in the first region, and the second filter allows transmission of infrared light therethrough to measure the second property to be measured in the second region.

* * * * *